United States Patent
Brandl et al.

(10) Patent No.: US 9,855,378 B2
(45) Date of Patent: Jan. 2, 2018

(54) MULTI-CHAMBER BAG

(75) Inventors: Matthias Brandl, Bad Koenigshofen (DE); Philippe Laffay, Sainte Foy les Lyon (FR); Michael Herrenbauer, Neu-Anspach (DE); Thomas Fichert, Warendorf (DE); Franz Kugelmann, Wendel/Bliesen (DE); Joern Hoermann, Heusweiler (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 700 days.

(21) Appl. No.: 13/495,743

(22) Filed: Jun. 13, 2012

(65) Prior Publication Data
US 2012/0310150 A1 Dec. 6, 2012

Related U.S. Application Data

(63) Continuation of application No. PCT/EP2010/069795, filed on Dec. 15, 2010.

(30) Foreign Application Priority Data

Dec. 16, 2009 (DE) .................. 10 2009 058 445

(51) Int. Cl.
*A61M 1/00* (2006.01)
*A61M 1/16* (2006.01)
(Continued)

(52) U.S. Cl.
CPC .......... *A61M 1/1656* (2013.01); *A61J 1/2093* (2013.01); *A61M 1/167* (2014.02);
(Continued)

(58) Field of Classification Search
CPC ........ A61M 1/1656; A61M 2205/3569; A61M 2205/6018; A61M 1/1666
(Continued)

(56) References Cited

U.S. PATENT DOCUMENTS 2,103,389 A * 12/1937 Salfisberg .......... B65D 75/5811
156/183
4,610,782 A 9/1986 Tersteegen et al.
(Continued)

FOREIGN PATENT DOCUMENTS

DE 198 25 158 C1 4/1999
JP 2005-67730 A 3/2005

OTHER PUBLICATIONS

International Search Report dated Apr. 28, 2011 of international application PCT/EP 2010/069795 on which this application is based.

*Primary Examiner* — Phillip Gray
(74) *Attorney, Agent, or Firm* — Kilyk & Bowersox, P.L.L.C.

(57) ABSTRACT

Method of dissolving/mixing of a concentrate in/with a fluid in a multi-chamber bag and a method for the production of a medical fluid, in particular a dialysis fluid, in a multi-chamber bag. Moreover, the multi-chamber bag itself is disclosed. In all embodiments, at least two different concentrates can be included separately in powder form, liquid form or semi-liquid slurry form for dissolution in a fluid in the multi-chamber bag. In addition, the use of the multi-chamber bag in haemodialysis or peritoneal dialysis or a haemodialysis or peritoneal dialysis device, in particular as a container for a dialysis fluid in a haemodialysis or peritoneal dialysis device, is described.

19 Claims, 5 Drawing Sheets

(51) Int. Cl.
*A61J 1/20* (2006.01)
*A61M 1/28* (2006.01)
*A61J 1/10* (2006.01)

(52) U.S. Cl.
CPC .............. *A61M 1/1666* (2014.02); *A61J 1/10* (2013.01); *A61J 1/2024* (2015.05); *A61M 1/287* (2013.01)

(58) Field of Classification Search
USPC .................. 604/29, 6.11, 408–410, 416, 414
See application file for complete search history.

(56) References Cited

U.S. PATENT DOCUMENTS

| | | |
|---|---|---|
| 4,767,526 A | 8/1988 | Vantard |
| 6,007,529 A | 12/1999 | Gustafsson et al. |
| 6,398,771 B1 | 6/2002 | Gustafsson et al. |
| 7,875,015 B2 | 1/2011 | Pahlberg et al. |
| 8,343,129 B2 | 1/2013 | Falkvall et al. |
| 2010/0069817 A1* | 3/2010 | Falkvall .............. A61M 1/1656 604/6.11 |
| 2012/0323209 A1 | 12/2012 | Falkvall et al. |

\* cited by examiner

MULTI-CHAMBER BAG

CROSS REFERENCE TO RELATED APPLICATIONS

This application is a continuation application of international patent application PCT/EP 2010/069795, filed Dec. 15, 2010, designating the United States and claiming priority from German application 10 2009 058 445.5 filed Dec. 16, 2009, and the entire content of both applications is incorporated herein by reference.

FIELD OF THE INVENTION

The present invention relates to a method of dissolving/mixing of a concentrate in/with a fluid in a multi-chamber bag and to a method for the production of a medical fluid, in particular a dialysis fluid, in a multi-chamber bag. Moreover, the present invention relates to a multi-chamber bag itself. In all embodiments, at least two different concentrates can be included separately in powder form, liquid form or semi-liquid slurry form for dissolution in a fluid in the multi-chamber bag. The present invention also relates to the use of the multi-chamber bag in haemodialysis or peritoneal dialysis or a haemodialysis or peritoneal dialysis device, in particular as a container for a dialysis fluid in a haemodialysis or peritoneal dialysis device.

BACKGROUND OF THE INVENTION

Haemodialysis or peritoneal dialysis devices are known in various versions. The exchange of substances between the blood and the dialysis fluid takes place in a dialyzer which has a first flow path for the blood and a second flow path for the dialysis fluid, wherein both flow paths are normally separated from each other by a semi-permeable membrane. The first flow path is part of an extracorporeal blood circulation system with a feed line and a return line for the blood and also additionally a pump supporting the blood flow. The second flow path is connected to equipment feeding and removing the dialysis fluid.

In addition to the so-called single-path systems in which the continuously fed dialysis fluid passes through the dialyzer only once and is then discarded, so-called batch systems are known. U.S. Pat. No. 4,610,782 describes such a haemodialysis device, which operates with a fixed-volume container sealed off from the atmosphere, which is completely filled with fresh dialysis fluid prior to the start of the treatment. During operation, the fluid is pumped out of the container through the dialyzer and the used fluid is passed back into the container.

Fresh and used dialysis fluid are prevented from mixing in the case of the known haemodialysis device by removing the dialysis fluid in the upper area of the container and returning it in the lower container area. Underlaying the fresh dialysis fluid with the used dialysis fluid remains stable through the maintaining of a vertical temperature gradient in the container from top to bottom.

The container consists of glass which, because of the pore-free surface, is superior with regard to hygiene and bacteriology compared to other materials. In addition, glass is largely resistant to chemicals coming into consideration, can be satisfactorily cleaned and is physiologically harmless. However, such a repeatedly re-usable glass container proves to be disadvantageous because the glass container needs to be disinfected before the renewed dialysis, treatment.

U.S. Pat. No. 4,767,526 likewise describes a dialysis device in which the dialysis fluid is provided in a container. In order to avoid disinfection, it is proposed to line the container with a flexible bag, which is discarded after use.

Flexible plastic bags which consist of two films lying flat one over the other and welded together at their edges are known as containers for holding medical fluids.

DE 198 251 58 C1 likewise describes a disposable bag for a haemodialysis device or a device for peritoneal dialysis which preferably has a concentrate for the preparation of dialysis fluid. This bag can consist of a chamber in which the used fluid is layered underneath the fresh dialysis fluid in the course of the dialysis process. Alternatively, the disposable bag can also contain a film which divides the bag into two chambers, wherein the fresh dialysis fluid is present in one chamber of the bag and the used fluid is passed into the other chamber during the dialysis process.

A disadvantage of the above-named glass containers is that a rapid re-use is not possible because of the laborious disinfection step. However, disposable bags, which do not have this disadvantage, have not yet solved the problem that in the case of introduced granular material to be dissolved in water the different constituents of the granular material react with each other during the storage of the bag including granular material, with the result that there is no storage stability over a certain period of time. In addition, dialysis fluids which are prepared by dissolving granular material which contains all the necessary constituents often have the problem that, as a result of an undesired reaction of different constituents, not all of the granular material dissolves. Both problems before-mentioned often lead to a degradation or agglomeration of at least one of the concentrates provided. Furthermore, it is important to correspondingly control the pH while the solvent is being poured into the bag with granular material, so that undesired precipitations are avoided during the dissolution of the granular material in the fluid. If the named problems occur, the dialysis fluid is not suitable for haemodialysis or peritoneal dialysis and must be discarded together with the bag.

In addition to glucose, or other ingredients which are not able to contribute to the electric conductivity of a fluid, and physiologically essential salts, or ions, dialysis fluids must have a pH in the neutral range. A pH in the neutral range is set by adding an acid and a basic component. These acid and basic components must necessarily be physiologically compatible. Therefore, carbonate salts, e.g., sodium hydrogen carbonate, are preferably used as basic buffer component. The solution must contain calcium and magnesium ions, in addition to sodium and potassium ions, as physiologically essential ions. A dialysis fluid is most often prepared from a single concentrate, which is introduced in the inlaid bag in the case of DE 198 25 158. If such concentrates which contain readily soluble calcium or magnesium salts and, as basic buffer component, a (bi)carbonate salt are stored for prolonged time, then the problem arises, at least under atmospheric humidity conditions, that the components can react with each other and thus form poorly soluble calcium or magnesium carbonate. Likewise, poorly soluble calcium or magnesium carbonate precipitates from a solution the pH of which is not set in the ideal range of preferably <pH 8. It is therefore disadvantageous to introduce a concentrate with all the necessary physiologically essential components in a bag together, since such systems cannot be stored for long because of the above-named problems and, further, because during dissolution in a fluid, sections of the solution have a pH greater than 8, with the result that undesired precipitations occur.

SUMMARY OF THE INVENTION

It is therefore an object of the present invention to provide a method of dissolving/mixing a concentrate in/with a fluid, a method for the production of a medical fluid by dissolving concentrates or a disposable bag which has inter alia the following advantages:
  high user-friendliness through an all-in-one concept and high application safety;
  high flow rates during the filling with fluid;
  low materials usage;
  optimum/rapid dissolution of the concentrates;
  avoidance of contamination through laborious connection of individual components for the preparation of the solution;
  storage stability of the raw materials (i.e. no glucose decomposition, degradation or agglomeration, no conversion of dicarbonates into $CO_2$, no calcium carbonate precipitations);
  controlled preparation of a solution from dry concentrates by sequential dissolution of the different dry concentrate components, wherein the formation of calcium carbonate precipitations can be prevented and the desired pH can be set;
  storage stability of the solution after the preparation from dry concentrates, without calcium carbonate precipitations occurring during storage and with the result that the pH remains stable in the solution; and
  finding a way of measuring by standard methods whether a concentrate which does not contribute to the electric conductivity of a medical solution is solved in a fluid (explanation: usually the concentration of a compound in solution is measured by its conductivity since in the case of electrolytes the concentration is proportional to the change in conductivity; however some essential substances for medical solutions may not be measured by this method, since they do not contribute to the conductivity).

In a first embodiment of the present invention, the named objects are achieved by a method of dissolving/mixing a concentrate in/with a fluid having the following steps:
  (a) providing a concentrate (5) in a chamber of a multi-chamber bag, wherein the chambers (2, 3) of the multi-chamber bag are separated from each other by a separating device (4, 4*a*),
  (b) introducing a fluid into one of the chambers (2, 3) of the multi-chamber bag,
  (c) breaching of the separating device (4, 4*a*) between the chambers (2, 3) of the multi-chamber bag by introducing the fluid, and
  (d) dissolving/mixing of the concentrate (5) in/with the fluid.

In other words, the above mentioned method is a method of preparing a dialysis fluid with the previously named steps (a) to (d). In a preferred embodiment, the dialysis fluid is a sterile dialysis fluid.

The method of the first embodiment is in the following referred to as "first method" according to the invention.

In a further embodiment of the present invention, the concentrate is preferably provided in a type B chamber of the multi-chamber bag which comprises one type A chamber and one type B chamber. It is preferred that the multi-chamber bag of the first method contains at least two, more preferred three and most preferred four type B chambers. Preferably two of the type B chambers are chambers which open at the same time or one opens before the other opens when the fluid is introduced, preferably in the type A chamber. Preferably the type A chamber does not contain a concentrate, and one type B chamber contains a first concentrate as defined below, and one type B chamber contains a concentrate with the acid component as defined below. It is preferred that the chamber with the first concentrate opens before or at the same time as the chamber opens containing the concentrate with the acid component. A third or fourth type B chamber may contain a concentrate with the basic component as defined below. It is further preferred that these chambers are opened later than the first and second type chambers from the point avoiding decomposition, degradation or agglomeration of the first concentrate.

A further embodiment of the present invention refers to a method for the production of a medical fluid having the following steps:
  (e) providing a multi-chamber bag (1) comprising a type A chamber (2), a first type B chamber (3) and a second type B chamber (3*a*), wherein the first type B chamber comprises a first concentrate (5) which does not contribute to the electric conductivity of the medical fluid and the second type B chamber comprises a second concentrate (5*a*) which contributes to the electric conductivity of the medical fluid, wherein the first type B chamber and the second type B chamber are each separated from the type A chamber by separating devices (4, 4*a*),
  (f) introducing a fluid into the type A chamber,
  (g) breaching of the separating devices between the chambers by introducing the fluid, and
  (h) dissolving/mixing of the concentrates in/with the fluid,
  wherein by the introducing of the fluid, the separating device of the first type B chamber is breached before or, even more preferred, at the same time as the separating device of the second type B chamber is breached.

The method for the production of a medical fluid mentioned before is herein referred to as "second method" according to the present invention.

A medical fluid in the sense of this invention is a fluid which is physiologically compatible, such as a dialysis fluid.

In the second method it is preferred that the first type B chamber is separated from the second type B chamber by an interspace which is constituted by a part of the type A chamber, i.e. the separating devices of both type B chambers are separating these chambers from the type A chamber individually.

All concentrates of the present invention may be concentrates in powder form, liquid form or semi-liquid slurry form, preferably in powder form.

All preferred embodiments of the present invention are referred to as belonging to the first and the second method, unless stated otherwise.

The differentiation of the chambers of the multi-chamber bag into "type A chamber" and "type B chamber" is to be understood to mean that the multi-chamber bag consists of at least two chambers in case of the first method, and of at least three chambers in the case of the second method. These two/three chambers can be the same in one embodiment according to the invention, or perform the same function in the bag, and different in another embodiment according to the invention, such as is seen from the following embodiments. If, in the following embodiments, there is more than one type B chamber, then this covers chambers which have the same operating mode and can have the same form, but also different forms.

Water, in particular RO (reverse osmosis) water, is preferably used as fluid. However, any differently demineralized water which is suitable for the preparation of physiologically compatible fluids can also be used.

In addition to the type A chamber and the type B chamber(s), the multi-chamber bag can also comprise further type B chambers. In preferred embodiments, the multi-chamber bag contains one type A chamber and a total of two type B chambers or one type A chamber and a total of three or four type B chambers. Each of the chambers, thus also the further type B chambers, is separated from each of the other chambers by separating devices. The separating devices are breached by introducing the fluid. Preferably each of the type B chambers has its own separating device so that between the separating devices of the type B chambers is at least a part of the type A chamber.

In the first method, the type A chamber may contain a concentrate in powder form, liquid form or semi-liquid slurry form. In the first method, the type B chamber of the multi-chamber bag can likewise also contain a concentrate in powder form, liquid form or semi-liquid slurry form. In case of the second method, it is preferred that the type A chamber does not contain a concentrate, but preferably both type B chambers comprise a concentrate. In the first and second method, if the multi-chamber bag contains one or more further type B chambers, it is preferred that these also contain a concentrate in powder form, liquid form or semi-liquid slurry form.

If the multi-chamber bag preferably contains a total of at least three chambers, concentrates of the same or different composition can be present in these. It is particularly preferred that the concentrates have different compositions. However, it is also conceivable that if there is a total of three or more chambers a concentrate of the same composition is present in two or more chambers.

It is particularly preferred in all embodiments of the present invention that the multi-chamber bag comprises at least a first and a second concentrate, as for example defined in the case of the second method, but is also preferred in the first embodiment. The first concentrate is thereby preferably a concentrate which does not contribute to the electric conductivity of the resulting (medical) fluid. The second concentrate is thereby preferably a concentrate which contributes to the electric conductivity of the resulting (medical) fluid. The first concentrate is thereby a substance which is not able to dissociate in solution into anions and cations or is a substance which is present in such a low amount that the contribution to the conductivity is not characteristic. These substances may be: pharmaceuticals, active ingredients, or in particular in the field of dialysis: osmotics, such as glucose, fructose, galactose, sorbitol, amino acids, polmeric osmotics such as maltodextrine, icodextrine and polyethylene glycol, or acids such as citric acid, lactic acid, succinic acid, fumaric acid and oxalic acid. The second concentrate is thereby a concentrate comprising a compound which is able to dissociate into anions and cations, such as for instance electrolytes.

Because of the previously named breaching of the separating device(s) between the type A chamber and the type B chamber(s), a resulting chamber forms, the volume of which comprises the sum of the volumes of the type A chamber and the type B chamber(s). In this way, granular material from different chambers can be dissolved in the fluid together through the introduction of the fluid, with the result that separately stored concentrates come into contact with each other only when the fluid is prepared. In other words, because of the breaking open or breaching of the separating device(s), a resulting chamber forms in which all the concentrates/the concentrate are/is dissolved in the solvent.

In a further embodiment, in particular of the first method of the present invention, the bag preferably comprises one type A chamber and two type B chambers, wherein each of the chambers contains a concentrate different from each of the other concentrates.

In case of the second method of the present invention, the type A chamber does not contain a concentrate and both the first and the second type B chambers contain different concentrates, namely the first and the second concentrate mentioned above.

In a further embodiment of the present invention, the bag preferably comprises one type A chamber and three type B chambers, wherein each of the three type B chambers contains a concentrate different from each of the other concentrates. In this case one concentrate is preferably the first concentrate, and the other concentrates are concentrates that contribute to the electric conductivity of the resulting fluid, but preferably different from each other.

It is particularly preferred that the bag contains two or more different (one first and one or more concentrates as the second concentrate) concentrates which are present separated in different chambers. The separation of the different concentrates has the advantage that the components of the concentrates do not affect each other, with the result that an adequate storage stability is ensured. The second concentrate may be a concentrate of an acid component or a concentrate of a basic component as defined below. The second concentrate is preferably a concentrate comprising glucose or is existing of glucose without any acid component. The concentrates can be present in liquid form dissolved in a liquid, preferably RO water or a physiologically compatible water, but also in dry form as powder or granular material, as well as in the form of semi-liquid slurry concentrates. Particularly preferably, the concentrates are present in dry form or as semi-liquid slurry concentrates. Any physiologically compatible acid is conceivable as acid component, citric acid, hydrochloric acid, acetic acid, succinic acid, fumaric acid, malic acid, lactic acid and amino acids being preferred. Citric acid is particularly preferably used. The basic component, or buffer component, is preferably a bicarbonate of an alkali salt, preferably sodium hydrogen carbonate. The concentrate of the acid component can additionally also contain physiologically compatible/necessary salts, such as sodium chloride, potassium chloride, calcium chloride or magnesium chloride. In addition to the basic or buffer component, the concentrate of the basic or buffer component can also contain metal salts, preferably sodium chloride and/or potassium chloride. In a particularly preferred embodiment, the concentrate of the acid component contains sodium chloride, potassium chloride, calcium chloride, magnesium chloride and citric acid. It is most preferred that the concentrate of the acid component comprises potassium chloride, calcium chloride, magnesium chloride (preferably anhydrous) and citric acid. The concentrate of the basic or buffer component preferably contains sodium chloride and sodium hydrogen carbonate. If the bag contains only two separate chambers, or two different concentrates in these chambers, then one or also both of the concentrates can contain glucose in addition to the named components. To avoid undesired glucose decomposition during the storage of the bag filled with concentrates, it is particularly preferred that the bag contains a total of three or more chambers, with the result that three different concentrates are present separated in different chambers. Then, in case of the first method, one concentrate can be introduced in the type A chamber and the two further concentrates in each case in a type B chamber. Alternatively, the type A chamber can also be unfilled (preferably in the second method) and the three different concentrates can be introduced into a total of three type B chambers. However, it is also possible that there is a total of five chambers, namely one type A chamber and four type B chambers, wherein the type A chamber is unfilled and two type B chambers are filled with the same concentrate and the two further type B chambers each contain a further concentrate. The provision of three separated concentrates has the advantage that glucose does not have to be introduced into a chamber together with the acid or basic, or buffer, concentrate. This is advantageous with regard to the resistance of the concentrates to glucose decomposition, degradation or agglomeration during storage.

The proportions of acid to basic component should be chosen such that during the dissolution of the concentrates the pH is preferably less than 8 but greater than 6, preferably in the range from 6.5 to 7.8, more preferably in the range from 6.8 to 7.6, even more preferably in the range from 7 to 7.5. Too high a pH is disadvantageous, as calcium and magnesium salts precipitate as calcium carbonate or magnesium carbonate. This is also why the calcium or magnesium salts should not be kept in the basic concentrate. Too low a pH is likewise disadvantageous, as otherwise carbon dioxide is released from the hydrogen carbonate, which in turn leads to an increase in the pH, which is disadvantageous for the previously named reason.

If sodium hydrogen carbonate is used in the basic concentrate and citric acid is used as acid component in the acid concentrate, then citric acid and sodium hydrogen carbonate are preferably present in a molar ratio range from 0.5:40 to 2:40.

The above-named quantities of the named components in the concentrates should be chosen such that by adding a certain quantity of solvent, in particular physiologically compatible water, the specific electric conductivity of the resulting total solution lies in the range from 10,000 to 17,000 mS/cm$^2$, preferably 11,000 to 15,000 mS/cm$^2$, even more preferred 13,000 to 14,000 mS/cm$^2$, and most preferred 13,666 mS/cm$^2$. The electric conductivity in the range mentioned above is important for the preparation of medical fluids, such as dialysis fluid. The electric conductivity is measured by a conductivity meter at a fluid temperature of 20° C. and a pressure of 1013 mbar.

The bag (multi-chamber bag) in the above-named methods is preferably a film bag which preferably consists of a flexible plastic film. In a further embodiment, the film bag is preferably formed from a single-layer or multilayer plastic film, wherein the innermost film layer is a weldable film layer. The separating device between the type A chamber and the type B chamber(s) is preferably formed into a tear seam by welding two opposite inner film layers in the bag. Accordingly, in this embodiment, by tear seam is meant a linear welded joint of two opposite inner sides of the bag. The tear seam preferably runs in the bag such that the type B chamber(s) is/are present separated from the type A chamber and is separated from further type B chambers, preferably in the way defined above, i.e. the interior spaces of the chambers do not connect. This is likewise true for several possibly present type B chambers. However, when the fluid is introduced, the separating device(s) is/are breached, with the result that the previously separated spaces connect.

In a further embodiment of the present invention, it is preferred that the fluid is introduced into the type A chamber. By introducing the fluid into the type A chamber, a force ("swell pressure") acts on the tear seam which separates the chambers from each other, with the result that the tear seam opens along the linear welded joint and a resulting chamber is formed the volume of which comprises substantially the sum of the volumes of all the chambers. The term "substantially" is here used to reflect the circumstance that, as a result of the presence of a tear seam in the multi-chamber bag, there can be small discrepancies between the volume of the resulting bag and the sum of the volumes of the chambers of the multi-chamber bag compared with the resulting bag (after the opening of the tear seam).

In a preferred embodiment of the present invention, the multi-chamber bag according to the first and the second method comprises all in all four type B chambers. The above mentioned first and second type B chambers are thereby designed in a way that their separating devices open before the separating devices of the third and the fourth chamber are opened. The first type B chamber preferably comprises a first concentrate as mentioned above. The second type B chamber preferably comprises a second concentrate which is preferably the concentrate of the acid component. The third and the fourth chamber preferably both comprise a second concentrate which is a concentrate of the basic component.

In a further alternative embodiment of the above-named first method, the type B chamber(s) is/are formed by an inner bag inside of the type A chamber which represents the separating device. In other words, inside the type A chamber, the outer limit of which substantially represents the outside of the multi-chamber bag, there are further bags which the type B chamber(s) represent(s). In this further alternative embodiment with so-called inner bags which represent the type B chamber(s), the fluid is preferably introduced into this inner bag. In addition, the fluid can also be introduced into the type A chamber, in order to possibly introduce fluid there, or to dissolve a possibly present concentrate in the type A chamber by this fluid, before the type B chamber(s) open(s) and the concentrate found therein enters the type A chamber in dissolved or semi-dissolved or undissolved form. The breaching of the separating device(s) of the type B chambers which are produced in the form of inner bags in the multi-chamber bag takes place by tearing open a tear seam present on the wall of the further inner bag(s). In other words, the inner bag(s) forming the type B chamber(s) has/have a tear seam which is preferably in the form of a perforation. By introducing fluid into the type B chamber(s), a pressure acts on the tear seam which causes this to tear, and the concentrates present in the type B chambers, together with the fluid, enter the resulting bag and there form a solution with the concentrates.

Preferably, the tear seams of the bag/inner bags are so-called peel seams. These are preferably produced by heat treatment and the joining of two opposite film sections. Peel seams have the advantage that they are generally soluble without a film rupture.

Preferably, the walls of the bag/inner bag have, in the region of the peel seam, a peel seam strength in the range from 0.2 to 15 N/15 mm, particularly preferably in the range from 0.3 to 11 N/15 mm, extremely preferably in the range from 0.5 to 8 N/15 mm. By "peel seam strength" is meant the tensile stress at the moment of the tearing of the peel seam. The peel seam strength can be determined by the known methods ASTM D 1876-01, ASTM F88-07 or on the basis of EN ISO 527-3. For this in the present application, the force with which a strip of film 15 mm wide tears along the peel seam was measured in newtons. The strip of film here is a T-shaped test strip. The peel seam is here located lengthwise to the width of the strip.

In case the multi-chamber bag of the methods of the present invention, in particular that of the second method, contains two type B chambers, it is preferred that a first type B chamber contains a concentrate which does not contribute to the electric conductivity of the fluid when solved therein. A deviation of 1 mS/cm, preferably 0.1 mS/cm, contributed by concentrate in a ready prepared solution is not regarded to be appropriate for a conductivity surveillance during solution manufacturing. The second type B chamber contains a concentrate which contributes to the electric conductivity of the fluid when solved therein. In this case the peel seam strength of the tear (peel) seam of the separating device of the first type B chamber is equal or lower, preferably lower than the peel seam strength of the tear (peel) seam of the separating device of the second type B chamber. This is also given for further type B chambers comprising concentrates which contribute to the electric conductivity of the fluid when solved therein. It is, however, particularly preferred that the further type B chambers are opened later then the first and the second type B chambers.

The fact that the peel seam strength of the first type B chamber is at most as high as the peel seam strength of the other type B chambers leads to the advantage that the release of the concentrate (first) which does not contribute to the electric conductivity can indirectly be measured by the conductivity change when the concentrate (second) is released which contributes to the conductivity, since due to the equal or lower peel seam strength, the first concentrate is released latest to the fluid when the second concentrate is released to the fluid. In this manner it can be ensured that the first concentrate is always solved in the fluid before or at the same time as other concentrates are solved in the fluid.

To achieve a rapid filling rate accompanied by the dissolution of all the concentrates, it is advantageous if the bag tapers conically or in the shape of a V towards its lower end. Preferably, the cone has an angle in the range from 30° to 75°, particularly preferably 45° to 65°, most preferably 55° to 65°. The fluid is introduced into the type A chamber or type B chambers through (a) feed opening(s) located at the upper end of the bag. It is advantageous for the purpose of the better dissolution of the concentrates in the type A chamber if a pipe runs from the feed opening in the upper area of the bag into the lower part of the bag, with the result that the fluid in the type A chamber enters the bag in the lower part. This is also true for the feed openings of the type B chambers which are present in the main bag in the form of the inner bags. To improve the dissolution of the concentrates, a spray nozzle is preferably attached to the lower end of the pipe, where the fluid emerges into the type A chamber. In addition, the pipe which leads through the feed opening into the inside of the type A chamber or the type B chamber(s) is preferably connected to the feed opening such that the only connection to the outside of the bag is through the pipe.

A further embodiment of the present invention by which the above-named object is achieved relates to a multi-chamber bag (bag) which preferably contains a type A chamber and at least one type B chamber, wherein the chambers are separated by a separating device, wherein at least sections of the separating device have a predetermined breaking point. By a predetermined breaking point is generally meant a point which breaks as a result of the application of a force and thus represents a breaching of a wall. In the present invention, by a predetermined breaking point is meant in particular a part of the separating device or a whole of the separating device which, through exposure to a force inside the chamber, causes the spaces of the chambers to come into contact with each other through the breaching of the separating device or of a part of the separating device (predetermined breaking point). Most particularly, by a predetermined breaking point is meant according to the invention an area within the bag which represents a part or a whole of the separating device. The predetermined breaking point is preferably formed by a peel seam. The peel seam preferably has a peel seam strength in the range from 0.2 to 15 N/15 mm, particularly preferably in the range from 0.3 to 11 N/15 mm, extremely preferably in the range from 0.5 to 8 N/15 mm. The peel seam strength is measured using the above-named methods.

All described embodiments in connection with the multi-chamber bag of the methods according to the invention may also be preferred embodiments of the multi-chamber bag according to the invention.

In a further embodiment, the bag according to the invention is preferably a bag which comprises a type A chamber, at least one type B chamber and at least two different concentrates in powder form and/or liquid form. The definition, named above with the methods according to the invention, of the concentrate(s) is also to apply to the concentrate(s) named here.

In the embodiment in which concentrates are already present in the bag, one of the concentrates is present in the type A chamber and another in a type B chamber, or two concentrates are present in type B chambers. The respective chambers are separated from each other by (a) separating device(s). At least sections of this (these) separating device(s) have a predetermined breaking point. This predetermined breaking point is defined just as above.

A further embodiment of the present invention is a multi-chamber bag which preferably comprises one type A chamber, a first type B chamber and a second type B chamber, wherein the first type B chamber comprises a first concentrate which is not able to contribute to the electric conductivity of a fluid wherein the concentrate is dissolved and the second type B chamber comprises a second concentrate which is not able to contribute to the electric conductivity of a fluid wherein the concentrate is dissolved. The three chambers are preferably separated from each other in a way as mentioned above. It is then particularly preferred that the peel seam strength of the peel seam of the predetermined breaking point of the separating device of the first type B chamber is equal or, preferably, lower than the peel seam strength of the peel seam of the predetermined breaking point of the separating device of the second type B chamber. This is advantageous from the point of solving the first concentrate in a fluid introduced into the bag without degradation or agglomeration. Should the multi-chamber bag contain further type B chambers, the peel seam strength of the peel seam of the predetermined breaking point of the separating device of the first type B chamber is preferably lower than the peel seam strength of the peel seam of the predetermined breaking point of the separating device of the further type B chambers.

The named bags are preferably film bags. Preferably, the bags according to the invention are made from a film which consists of one piece. In other words, the film defining the external dimensions of the bag is made from one piece of film. The bag according to the invention or the bag which is used in the above-named method is preferably sterile in its interior. The state of the materials and items achieved by a method by which the materials and items are freed of living microorganisms is referred to as sterile. In practice, however, a complete sterilization is not one hundred percent certain. Therefore, by "sterilization" or the term "sterile" is meant a reduction in the number of microorganisms capable of multiplying by a factor determined according to the field of use. Inter alia is meant by this that the residual level of microorganisms capable of multiplying in one unit of sterilizing product is at most 1CT6 colony-forming units, i.e. a maximum of one microorganism capable of multiplying may be contained in a million units of identically treated sterilizing product. The sterilization can be carried out by physical (thermal, irradiated) or chemical methods.

In a further embodiment of the present invention, the bag according to the invention consists of a single-layer or multilayer film. The innermost layer of the single-layer or multilayer film is preferably a weldable film layer. The separating device preferably comprises a tear seam which is formed by welding two opposite innermost film layers. By a tear seam is meant in this connection a tear seam such as is defined above in connection with the method according to the invention. The tear seam is preferably a peel seam.

In an alternative embodiment, the separating device is formed by forming in the bag one or more further inner bags inside the type A chamber which represent the type B chambers. In this embodiment, the type A chamber can contain a feed opening for the fluid, but the inner bag(s) inside the type A chamber which form(s) the type B chambers can also have feed openings through which the fluid is introduced into the inside of the type B chambers. By introducing the fluid, a pressure acts on the wall of the bag of the type B chamber(s) which preferably has/have a tear seam which is defined as above. Through this pressure, the separating device(s) or the wall(s) of the inner bag is/are breached, with the result that the contents of the type B chamber(s) enter the type A chamber, with the result that all of the dissolved or partly dissolved concentrates from the type B chambers enter the type A chamber and are mixed.

The volume capacity of the bags after the separating device(s) has/have been breached is 30 to 100 liters, preferably 40 to 90 liters, particularly preferably 50 to 80 liters and extremely preferably 55 to 70 liters.

As already mentioned above, the bag can contain a concentrate in powder and/or liquid form in at least two chambers in each case.

In a further embodiment of the present invention, the bag comprises one type A chamber and two type B chambers, wherein each of the chambers contains in each case a concentrate in powder and/or liquid form. These concentrates are preferably of different composition, wherein what was said above in connection with the method is also to apply to these concentrates and compositions.

In a further embodiment of the present invention, the bag according to the invention preferably comprises one type A chamber and three type B chambers, wherein the three type B chambers each contain a concentrate in powder and/or liquid form.

If the bag contains one type A chamber and two type B chambers, then there can be a concentrate, as defined above, with an acid constituent in one of the type B chambers and a concentrate with a basic or buffer constituent in one further type B chamber. In this case, glucose can be admixed with one or both concentrates. However, for the purpose of avoiding glucose decomposition, it is advantageous according to the invention to store the glucose in the form of a further concentrate in a separated chamber. In this case, in the embodiment of the three-chamber bag with one type A chamber and two type B chambers, the concentrate with the basic or buffer component is present in the type A chamber, and the concentrate with the acid component is present in one of the type B chambers and the glucose concentrate in the other of the two type B chambers. In the case of the bag with more than a total of three chambers, namely a bag which comprises one type A chamber and three or more type B chambers, the three different concentrates are preferably present in the type B chambers.

In the above-named embodiments of the bag, it is preferred that the first concentrate is first of all dissolved by the fluid or is dissolved at the same time as the concentrate with the acid component. If the bag contains a total of three type B chambers in which the first concentrate, the concentrate with the acid component and the concentrate with the basic or buffer component are respectively located, then it is advantageous to arrange the chambers such that the first concentrate is dissolved first of all in the solvent, the concentrate with the acid component at the same time or second and the concentrate with the basic component last. This has the advantage that the pH remains stable in the above-named preferred range, and less $CO_2$ forms than is done otherwise. In an alternative embodiment a concentrate with the acid component is dissolved prior to a concentrate with the basic component. Evolution of $CO_2$ gas has to be considered and measures for compensating $CO_2$ pressures have to be taken into account. Sequential dissolution in the named order is also advantageous in order to ensure a homogeneous dissolution process. If dry concentrates are used, smaller concentrate components dissolve more quickly and the risk of agglutination is less. The sequential dissolution of the concentrate components is achieved by opening the individual chambers in sequence. The sequential opening of the chambers (preferably of type B) can be achieved by targeted actuation of the chambers with internal filling pressure (swelling pressure). In the case where the chambers of the multi-chamber bag are formed by welding opposite inner film sides of the bag, the bag fills from below through the feed line of the type A chamber. In an embodiment, in which there are more type B chambers, the chamber arranged furthest down is opened first owing to the pouring of the solvent into the type A chamber—owing to the filling pressure (swelling pressure) on the peel seam. The chronological order of the loosening/breaking open of the peel seam can be controlled through the corresponding arrangement of the chambers. Thus the sequential addition of concentrate to the resulting chambers forming because of the opening of the peel seam can be ensured. 2, 3, 4 or 5 chambers (of type B) can thus be arranged, offset one above the other, which tear open in succession. The loosening process is thus easily controlled through the bag design.

In the first method of the present invention, it may also be preferred that the first concentrate is first of all dissolved by the fluid or is dissolved at the same time as the concentrate with the acid component. If the bag contains a total of three type B chambers in which the first concentrate, the concentrate with the acid component and the concentrate with the basic or buffer component are respectively located, then it is advantageous to arrange the chambers such that the first concentrate is dissolved first of all in the solvent, the concentrate with the acid component at the same time or second and the concentrate with the basic component last.

In the named embodiments, the volume of the type A chamber can be a multiple of the volumes of the type B chambers.

After the process of filling the multi-chamber bag with the fluid is concluded, the chamber resulting after the breaching of the separating devices comprises a volume which substantially corresponds to the volumes of all the chambers of the multi-chamber bag, namely to that of the type A chamber and the type B chamber(s). The volume of the type A chamber of the multi-chamber bag preferably comprises a large part of this resulting chamber in which the solution or suspension is located after the breaching of the separating devices. In this case, the type A chamber preferably has a volume which is 1 to 20 times (preferably 2 to 18 times, particularly preferably 3 to 15 times, still more preferably 4 to 12 times, most preferably 5 to 10 times) greater than the sum of the volume(s) of the type B chamber(s).

In all of the named embodiments, the size of the type B chambers is preferably determined by the volume of the concentrates contained therein, but it can also be 1 to 4 times larger (preferably 2 to 3 times larger) than the volume of the concentrate requires. Very generally, it should also be noted at this point that, when the type B chamber(s) is/are being filled with fluid, the loosening process is already taking place partly in the type B chamber(s), without the separating device already being breached. This pre-loosening process can be optimized through a suitable choice of the hypothetical empty volume of the type B chamber(s) compared with the volume of the concentrate. The larger the volume of the chamber compared with the volume of the concentrate, the better the performance of the pre-loosening process can be (given constant tear strength of the separating devices).

In an alternative embodiment, however, the volume of the type A chamber can also not be a multiple of the sum of the volume(s) of the type B chamber(s), but be exactly as large as or smaller than the volume of one of the type B chambers. In this case, the dimensions of the type A chamber preferably do not differ substantially from those of the type B chamber(s). One chamber is connected to the next (type A chamber and type B chamber(s)) via separating devices. The type A chamber can lie next to one or more type B chambers, but also between two or more type B chambers. In this way, the type A chamber is indistinguishable from type B chambers. Through the simultaneous or successive breaching of the separating device(s) during filling with fluid, a resulting chamber forms, the volume of which substantially comprises the sum of the volumes of all the chambers of the multi-chamber bag. In the case of a bag which comprises more than two chambers, the contents of the first chamber, together with the fluid, are introduced into the second chamber preferably lying beneath it, during the successive breaching of the separating devices. The subsequent breaching of the second separating device then leads to the combined contents of the first and the second chamber being introduced into the third chamber preferably lying beneath it, and so on (as appropriate). Preferably, the fluid is poured with an above-named feed device into the type A chamber, which is then the first chamber in the above-named embodiment, which is preferably arranged higher up than the type B chambers. In this case, the type A chamber can be distinguished from the type B chamber(s) in particular by this feature.

In the case where the type B chambers are formed by inner bags in the type A chamber of the bag, the arrangement of the inner bags is of less importance, as the peel seams do not split open as a result of the filling of the type A chamber with fluid, but are opened by filling the respective type B chamber with fluid. As a result of the filling, a filling pressure (swelling pressure) acts on the peel seam of the inner bag forming the type B chamber. If the filling pressure reaches a certain level, the peel seams open and the respective concentrate-fluid mixture/solution enters the type A chamber. As regards the arrangement of several type B chambers, it only needs to be borne in mind that the contents of a chamber arranged higher up do not pour out over an inner bag of a further type B chamber. In this way, an incomplete dissolution of the corresponding concentrate is avoided. The sequential opening of the type B chambers in the above-named order is either ensured by the peel seams having correspondingly graduated different peel seam strengths with the same rate of filling the type B chambers with fluid, or by the fluid being introduced into the type B chambers in sequence with the same peel seam strengths.

All of the features named with regard to the multi-chamber bag according to the invention are also features which the multi-chamber bag can have in the above-named method according to the invention.

In addition, it is advantageous with regard to the dissolution rate or the dissolution behavior of the concentrates in the bag that the bag tapers conically or in the shape of a V towards its lower side. The conical or V-shaped end of the bag is located on the opposite side of the feed opening of the bag. The cone preferably has an angle in the range from 30° to 75°, particularly preferably 45° to 65°, most preferably 55° to 65°. In addition, it is advantageous if a pipe is passed through the feed opening into the lower part of the bag, with the result that fluid to be introduced enters the bag in the type A chamber in the lower part. The pipe is normally connected to the feed opening such that the only opening to the outside of the bag is through the inside of the pipe. The pipe is preferably a plastic tube.

If one of the above-named bags according to the invention is used in haemodialysis or peritoneal dialysis, then the chamber resulting after the breaching of the separating devices, the volume of which substantially comprises the sum of the volumes of all the chambers, preferably represents a space for keeping fresh dialysis fluid. Through the named feed opening, which can also serve as an outlet opening, the freshly prepared dialysis fluid can be used in a haemodialysis or peritoneal dialysis device. The used dialysate can be collected in such a dialysis device either in a separated container or in a container surrounding the bag according to the invention. It is preferred that such a container surrounding the bag according to the invention is likewise a film bag which surrounds the whole of the outside of the bag according to the invention. A feed opening for the used dialysate into the surrounding bag preferably leads through a tube through the inlet or outlet opening of the bag according to the invention all the way through the type A chamber and ends in the bag surrounding the bag according to the invention which is to collect the used dialysis fluid. Preferably, the bag surrounding the bag according to the invention, which is to collect the used dialysis fluid, is made from the same material as the bag according to the invention.

A further embodiment of the present invention relates to the use of the bag according to the invention in haemodialysis or peritoneal dialysis, in particular as a container for keeping dialysis fluid in a haemodialysis or peritoneal dialysis device.

The bag used in the process according to the invention or the bag according to the invention or the inner bags preferably consist of a multilayer film. The multilayer film preferably has an elongation at tear in longitudinal direction of the extrusion of the film of 250% to 850%, preferably 400% to 800%, more preferably 500% to 750% and most preferably 600% to 700%, and in transverse direction of the extrusion of the film of 300% to 1050%, preferably 450% to 1000%, more preferably 600% to 900% and most preferably 700% to 800%.

By elongation at tear or elongation at break is meant the percentage ratio of the change in length AL (at break) to the starting length. It expresses the capacity of a material to follow changes in shape without cracking. Elongation at tear is measured in the tensile test according to DIN 53455.

A large capacity of the film to change its length in longitudinal direction of the extrusion of the film in the abovementioned range has the advantage according to the invention that, while it is being filled with or emptied of (used or fresh) dialysate, the bag undergoes a change in volume without forming cracks before the given upper limits.

This brings with it the further advantage that when unfilled only a small amount of material is required, but there is nevertheless a large volume capacity when filled. A product can thereby be provided which brings with it only a small amount of waste. This is particularly advantageous from environmental points of view.

By "multilayer film" is meant in the present invention a film which consists of two or more layers of different or the same material which are joined together by adhesion. It is preferred within the framework of the present invention that the multilayer film is built up of from 2 to 10 layers, wherein a structure of 2 to 5 layers is more preferred and a structure of 3 or 4 layers is particularly preferred. The multilayer film can be produced according to any process which is known to a person skilled in the art as suitable for the purpose according to the invention.

Furthermore, the multilayer film preferably has a tear strength in longitudinal direction of 300 N/mm$^2$ to 350 N/mm$^2$, preferably 310 N/mm$^2$ to 340 N/mm$^2$ and more preferably 320 N/mm$^2$ to 330 N/mm$^2$, and in transverse direction of the extrusion of the film of 220 N/mm$^2$ to 270 N/mm$^2$, preferably 230 N/mm$^2$ to 260 N/mm$^2$ and more preferably 240 N/mm$^2$ to 250 N/mm$^2$.

By "tear strength" is meant the tensile stress which is exerted on an item at the moment of tearing. Tear strength is measured in the tensile test according to DIN 53455. A tear strength below the above-named lower limit is disadvantageous, as the bag otherwise tears prematurely through overextension. Although the bag is very tear-resistant above the cited upper limit, it is not sufficiently extensible.

In addition, the multilayer film preferably has a transverse extension ratio $\mu$ in the rubber-elastic state of 0.45 to 0.55, more preferably 0.47 to 0.53 and most preferably 0.49 to 0.51.

The transverse extension ratio, also called Poisson's ratio, is defined as the ratio of relative change in thickness $\Delta d/d$ to the relative change in length $\Delta l/l$ upon exposure to an external force or stress.

In addition, the multilayer film can be extended by up to 500% by a force of preferably 45 N to 60 N, more preferably 48 N to 62 N, most preferably 52 N to 58 N. To measure the extensibility a weight which corresponds to a specific force in N is applied uniformly to a 15-mm wide film and the change in length measured.

A high extensibility has the advantage that the bag is small when unfilled and thus easy to handle. In addition, the material requirement is small as a result of the strong extensibility of the material. A simpler manufacture and packaging of the material is thus also made possible.

In the case of the bag according to the invention, the ratio of the external surface of the bag when filled to the maximum to the external surface when unfilled is preferably in the range of preferably 2/1, more preferably 5/1. Typical upper limits are approx. 8/1 to 12/1, e.g. 10/1 or 9/1. However, higher ratios are also provided for according to the invention.

By "external surface" is meant the surface of the bag which can come into contact with its surroundings (air) when filled and also when unfilled. The term "when filled to the maximum" is described by the maximum size of the bag at which the bag still just forms no cracks and consequently does not yet tear.

By "when unfilled" is meant the state of the bag in which the inside of the bag is essentially not filled by material of any kind, i.e. essentially occupies no space.

The property of the increase in surface in relation to the fill quantity ensures that the multilayer film of the bag is always under pressure during filling, with the result that as it is increasingly filled this pressure increases and any creases in the multilayer film which may be present when unfilled increasingly disappear. This has the advantage according to the invention that a crease-free introduction of the bag into a reservoir of a medical apparatus, in particular a dialysis machine, is ensured. Thus the complete removal of the fluid from the bag is also ensured.

In a further embodiment of the present invention, the ratio of the volume capacity of the bag according to the invention when filled to the maximum to the volume capacity in the state in which the multilayer film is unextended is preferably 3/1, more preferably 5/1. Typical non-limiting ranges are 3/1 to 12/1, more preferably 5/1 to 11/1, still more preferably 7/1 to 10/1 and most preferably 8/1 to 9/1. Other, higher upper limits are, however, also possible according to the invention.

By "volume capacity in the state in which the multilayer film is unextended" is meant the volume which can be poured into the bag without an extension of the multilayer film.

The above-named properties of the film (preferably multilayer film) are preferably achieved by a film of three or more layers, preferably three layers. Both of the external layers of the film are to be chosen from a material which prevents damage to these layers—for example due to the handling of the film—from triggering undesired predetermined breaking points, which lead to the tearing of the bag when the bag formed from this is subsequently filled and when the bag undergoes extreme extension. Accordingly, both of the external layers of the film, unlike the inner layer(s), are preferably more robust against mechanical influences. Furthermore, the film preferably must not tend to stick during the storage of a multi-chamber bag according to the invention and any heat sterilization. Opposed to this is the demand to produce peel seams with a corresponding welding tool preferably at relatively low temperatures. Peel seams are characterized in that they are produced by a partial welding or gluing of films by heat treatment and contact pressure. Preferably, therefore, the temperature for the formation of the peel seams lies below the welding temperature for permanent welded seams. A film which is used according to the invention should preferably have a high elastic extensibility without a high exposure to force.

However, such films tend in most cases to already form undesired gluing connections without a pressing-on effect of corresponding welding tools at a common heat sterilization temperature of 100 to 120° C., for 5 to 15 minutes (approx. 10 minutes) at a pressure between 1.5 and 2.5 bar (approx. 2 bar). A film for a bag according to the invention is therefore preferably to be a compromise between technically opposing requirements of heat sterilizability, mechanical robustness, elastic extensibility, producibility of permanent and peelable joining seams and good severability of the films after heat treatment. As regards the elastic extensibility of the film and of the bag produced therefrom, an even extension due to exposure to force or the filling of the bag is required. If the bag is extended unevenly, there is the risk that individual areas are over-extended while other areas are not, or less, extended.

That is, the multi-chamber bag according to the invention or multi-chamber bag of the methods according to the invention is preferably a film bag, wherein the film is an elastic extensible film which is preferably extended when the fluid is introduced into one of the chambers. The bag extends in a balloon-like way when filled with diluent and contracts when the fluid is extracted from the bag. The bag is manufactured from a film which shows an elastic strain behavior whereby plastic strain characteristics are preferably suppressed.

Exemplary film structures are:

Film type 1: Inner layer: layer thickness: 10 μm, 100 parts of hydrogenated styrene block copolymer of styrene, ethylene, butylene or propylene, e.g. SEBS Septon 2005, Kuraray, 70 parts random polypropylene with ethylene as comonomer PP23M10cs264 Rexene, Huntsmen Middle layer: layer thickness: 100 μm, 30% Tuftec 1221, Asahi, 70% analogous to the composition of the inner layer Outer layer: analogous to the inner layer Film type 2: Inner layer: layer thickness: 10 μm, random polypropylene 60% Bormed SC 220 Borealis, hydrogenated styrene block copolymer of styrene, ethylene, butylene or propylene, e.g. 40% Septon 8004, Kuraray Middle layer: 100 μm, 30% Tuftec H 1221, Asahi Outer layer: analogous to the inner layer Film type 3: Inner layer: layer thickness: 10 μm, 100 parts styrene block copolymer of styrene, ethylene, butylene or propylene, e.g. Septon 2005, Kuraray, 70 parts random polypropylene with ethylene as comonomer PP23M10cs264 Rexene Middle layer: layer thickness: 100 μm, 40% Engage, Dow Chemical, 25% Tuftec 1062, 35% Septon 8004, Kuraray Outer layer: analogous to the inner layer

BRIEF DESCRIPTION OF THE DRAWINGS

Five different embodiments of the bag according to the invention or of a bag which can be used in the method according to the invention are described in detail below with reference to the drawings wherein.

DESCRIPTION OF THE PREFERRED EMBODIMENTS OF THE INVENTION

Figure 1:
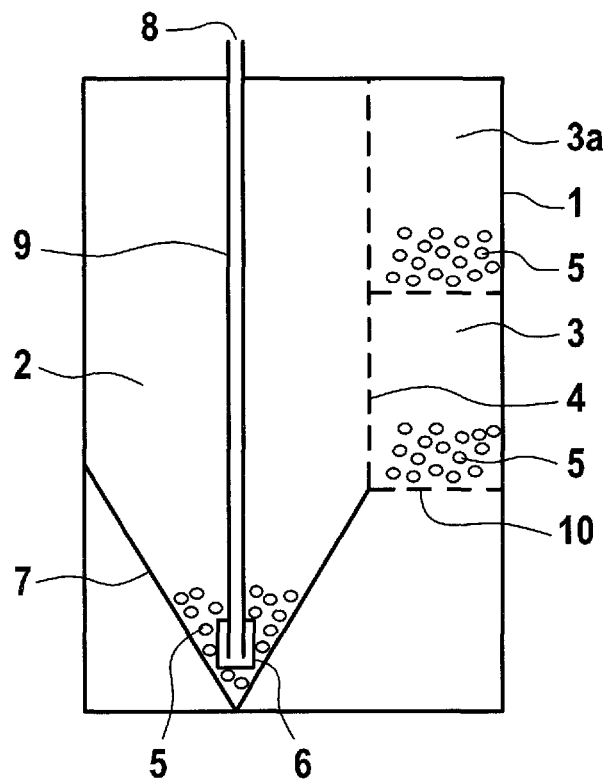
FIG. 1 is a section through a bag with one type A chamber and two type B chambers, wherein the separating device is present in the form of a tear seam.

FIG. 1 shows a section through a bag (1) with one type A chamber (2) and two type B chambers (3, 3a), wherein the separating device (4) is present in the form of a tear seam (10). There is a concentrate (5) which is preferably a basic or buffer concentrate in the type A chamber (2). A pipe or tube (9) leads from the feed opening (8) into the inside of the type A chamber (2) and ends in the lower V-shaped area of this chamber. At the end of the tube, there is a spray nozzle (6) through which the fluid enters the chamber. The welded seam (7) represents an internal welding of the inner surface of the bag film which can be a tear seam within the meaning of the invention or represents a welded seam which has no predetermined breaking point. The type A chamber (2) preferably contains a concentrate (5) with basic or buffer component, whereas the type B chambers (3, 3a) preferably contain the concentrate with glucose or the concentrate with the acid component (5).

Figure 2:
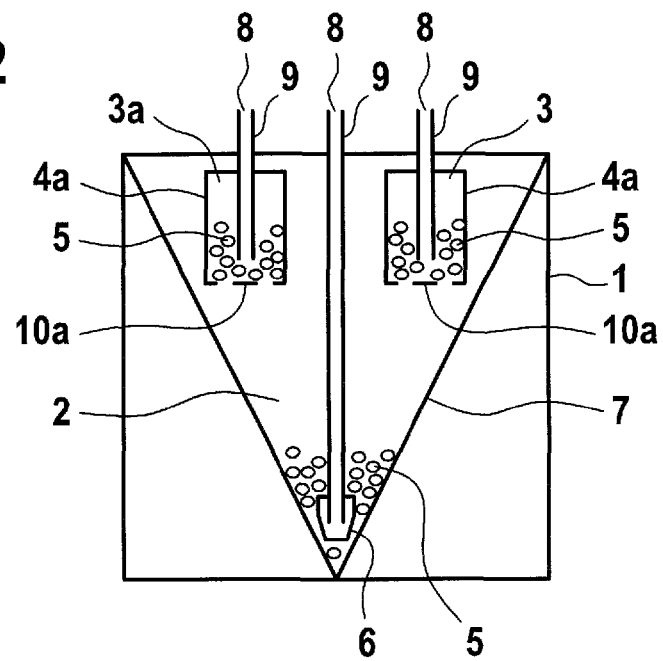
FIG. 2 is a section through a bag with one type A chamber and two type B chambers, wherein the separating device or the type B chambers are present in the form of a bag which has a predetermined breaking point in the form of a tear seam.

FIG. 2 shows a section through a bag (1) with one type A chamber (2) and two type B chambers (3, 3a), wherein the separating device (4a) or the type B chambers (3, 3a) are present in the form of an inner bag inside the type A chamber, wherein this bag has a predetermined breaking point in the form of a tear seam (10a). The type A chamber (2) and the type B chambers (3, 3a) have a feed opening (8). A fluid can be introduced into the inside of the chambers through this feed opening. The feed openings (8) are preferably present in the form of a pipe or tube (9) which extends into the concentrate (5) as far as the lower part of the chambers. A spray nozzle (6) which makes possible a better dissolution of the concentrate in the type A chamber (2) is preferably attached to the lower end of the pipe (9) of the type A chamber (2). The type A chamber (2) is preferably present in the shape of a V which tapers sharply downwards, with the result that, compared with a square bag, a better dissolution behavior of the concentrates in the type A chamber is made possible. The V shape of the type A chamber (2) is achieved by producing a welded seam (7) in the shape of a V through opposite inner sides of the bag. The welded seam can be a tear seam within the meaning of the invention, with the result that, from a certain pressure which is produced by the pouring in of a certain quantity of fluid, this splits open and provides a larger space in the form of a square bag. The concentrate (5) in the type A chamber is preferably a basic or buffer concentrate. The concentrates (5) in the type B chambers (3, 3a) are preferably a concentrate which contains glucose, or the concentrate which contains the acid component.

Figure 3:
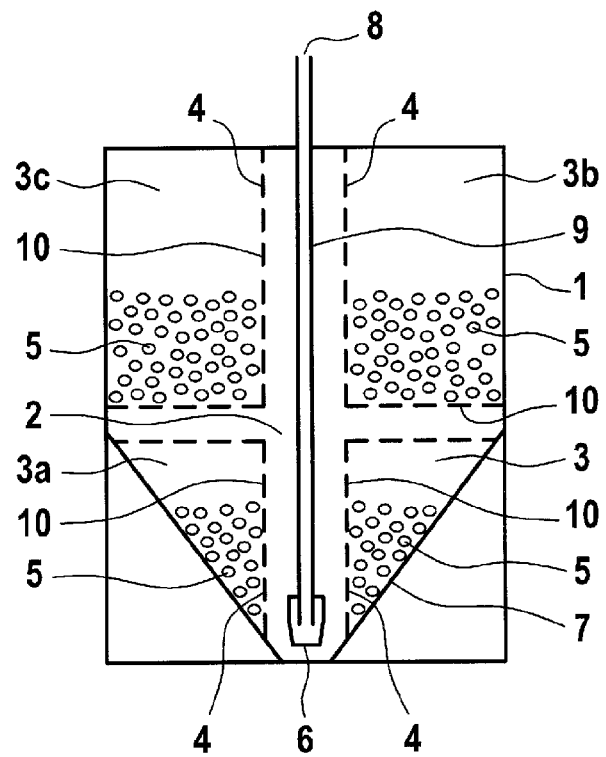
FIG. 3 is a section through a bag which has one type A chamber and four type B chambers, wherein the separating device is present in the form of a tear seam.

FIG. 3 shows a section through a bag (1) which has one type A chamber (2) and four type B chambers (3, 3a, 3b, 3c), wherein the separating device or separating devices (4) is/are present in the form of a tear seam (10). When the type A chamber (2) is being filled with fluid through the pipe or tube (9) through the feed opening (8), a force acts on the tear seams (10), with the result these open and firstly the concentrates (5) of the lower type B chambers (3, 3a) are dissolved first in the fluid introduced into the type A chamber (2) and the concentrates (5) of the type B chambers (3b, 3c)

are dissolved second in the fluid as a result of the tearing open of the tear seam (10) of these chambers. The pipe or the tube (9) which leads into the type A chamber (2) has, at the lower end of the V-shaped area of the bag, a spray nozzle (6) which ensures the better dissolution of the concentrates (5) in the fluid. Also, this bag (1) preferably has, in the lower area, a conical or V-shaped tapering end which is achieved by welding the inner opposite sides of the bag by a welded seam (7). This welded seam can be a tear seam within the meaning of the invention, which splits open under a corresponding pressure acting as a result of the pouring in of the fluid, with the result that a square bag forms, or a solid welded seam, whereby the V shape of the bag is preserved during the dissolution of the concentrates. The type B chambers (3, 3a) preferably contain the basic or buffer concentrate (5), whereas one of the type B chambers (3b, 3c) contains the glucose concentrate (5) or the concentrate (5) with the acid component.

Figure 4:
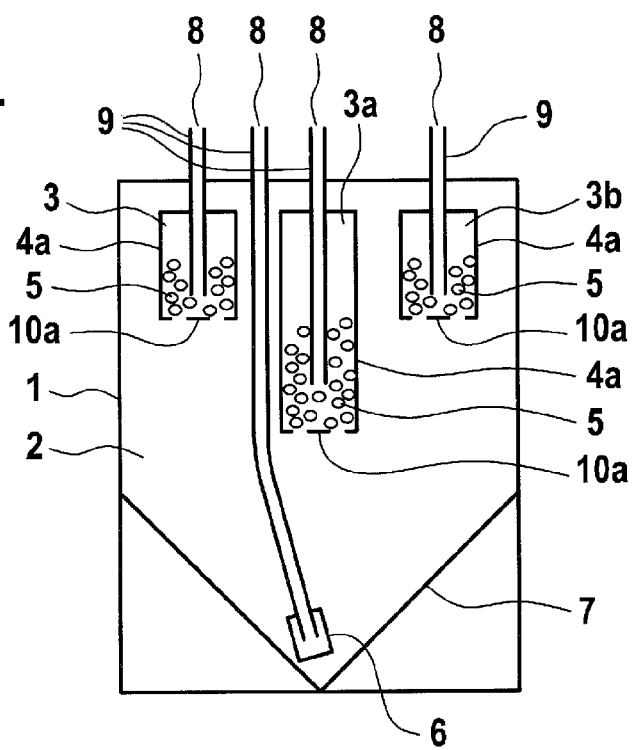
FIG. 4 is a section through a bag which has one type A chamber and three type B chambers, wherein the separating device(s) or the type B chambers are present in the form of inner bags which have a tear seam as predetermined breaking point.

FIG. 4 shows a section through a bag (1) which has one type A chamber (2) and three type B chambers (3, 3a, 3b), wherein the separating device(s) (4a) or the type B chambers (3, 3a, 3b) are present in the form of inner bags which have a tear seam (10a) as predetermined breaking point. Each of the type B chambers (3, 3a, 3b) and the type A chamber (2) have a feed opening (8) which makes it possible to introduce a fluid into the respective chambers through a pipe or a tube (9). The tube or the pipe (9) preferably extends, in the type B chambers (3, 3a, 3b), so far into the chambers that the fluid emerges in the middle of the concentrates (5). The tube or the pipe (9) of the type A chamber (2) leads into the lower end of the V-shaped, tapering bag and preferably has a spray nozzle (6) for the better dissolution of concentrates which enter the type A chamber. The type B chambers (3, 3a, 3b) each have a tear seam (10a) as predetermined breaking point, which is breached at a certain pressure exerted as a result of the introduction of the fluid, with the result that the concentrates (5) of the type B chambers (3, 3a, 3b) enter the type A chamber (2) together. The bag (1) surrounding the inner bags or type B chambers (3, 3a, 3b), which essentially forms the type A chamber (2), has a V-shaped form at the lower end. The V shape is achieved by welding two opposite inner sides of the bag by a welded seam (7). The welded seam can be a tear seam within the meaning of the invention, which is breached at a certain pressure caused by the introduction of the fluid, with the result that a rectangular bag is formed, or can be a fixed welded seam by which the V shape of the bag is preserved. The type B chamber (3a) preferably contains the concentrate with the acid or buffer component. Accordingly, the type B chambers (3, 3b) preferably contain the concentrate with the glucose component and the concentrate with the acid component.

Figure 5:
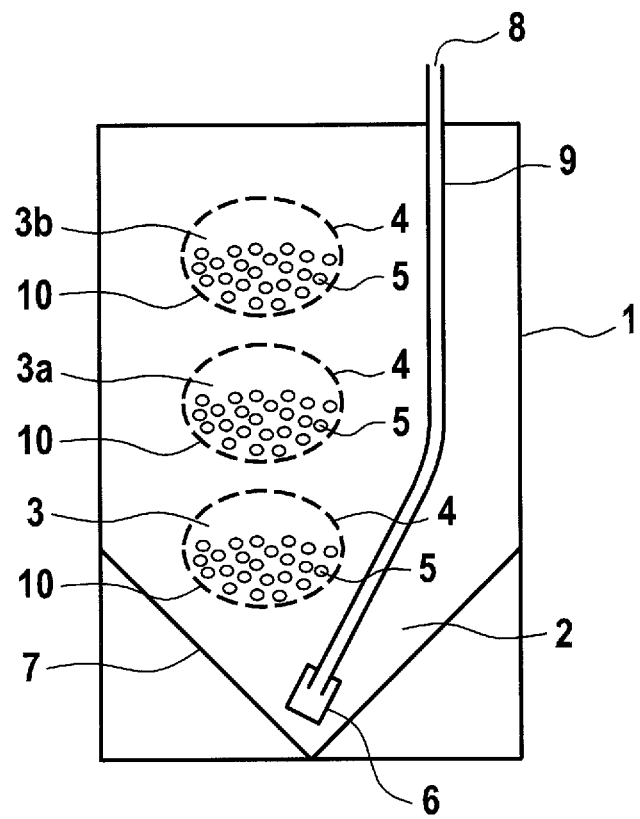
FIG. 5 is a bag with one type A chamber and three type B chambers, wherein the type B chambers are present separated from the type A chamber by a separating device in the form of a tear seam.

FIG. 5 shows a bag (1) with one type A chamber (2) and three type B chambers (3, 3a, 3b), wherein the type B chambers (3, 3a, 3b) are present separated from the type A chamber (2) by a separating device (4) in the form of a tear seam. The tear seam is formed by welding two opposite inner sides of the bag (1) together such that the tear seams split open as a result of a pressure caused by the pouring in of the fluid and the concentrates combine in the type A chamber (2). A pipe or tube (9) through which the fluid can enter the type A chamber (2) through a feed opening (8) extends into the inside of the type A chamber (2). A spray nozzle (6) is preferably located at the lower end of the pipe or tube (9) for the better dissolution of the concentrates in the fluid. The bag preferably tapers in the shape of a V at the lower end in the type A chamber (2), which is ensured by a welded seam (7). The welded seam (7) can be a tear seam within the meaning of the invention which is breached as a result of a pressure caused by the filling with the fluid, with the result that a rectangular bag forms, or it can be a fixed welded seam which ensures the V shape of the bag even when filling with fluid. The concentrate (5) in the type B chamber (3) is preferably a concentrate with a basic or buffer component. The concentrate (5) in the type B chamber (3a) is preferably a concentrate which contains glucose. The concentrate (5) in the type B chamber (3b) is preferably a concentrate with an acid component. Just as with the arrangements in FIGS. 1 to 4, such an arrangement ensures that the pH remains stable in the preferred range during the mixing of the different concentrates in the type A chamber in the range preferred according to the invention.

Figure 6:
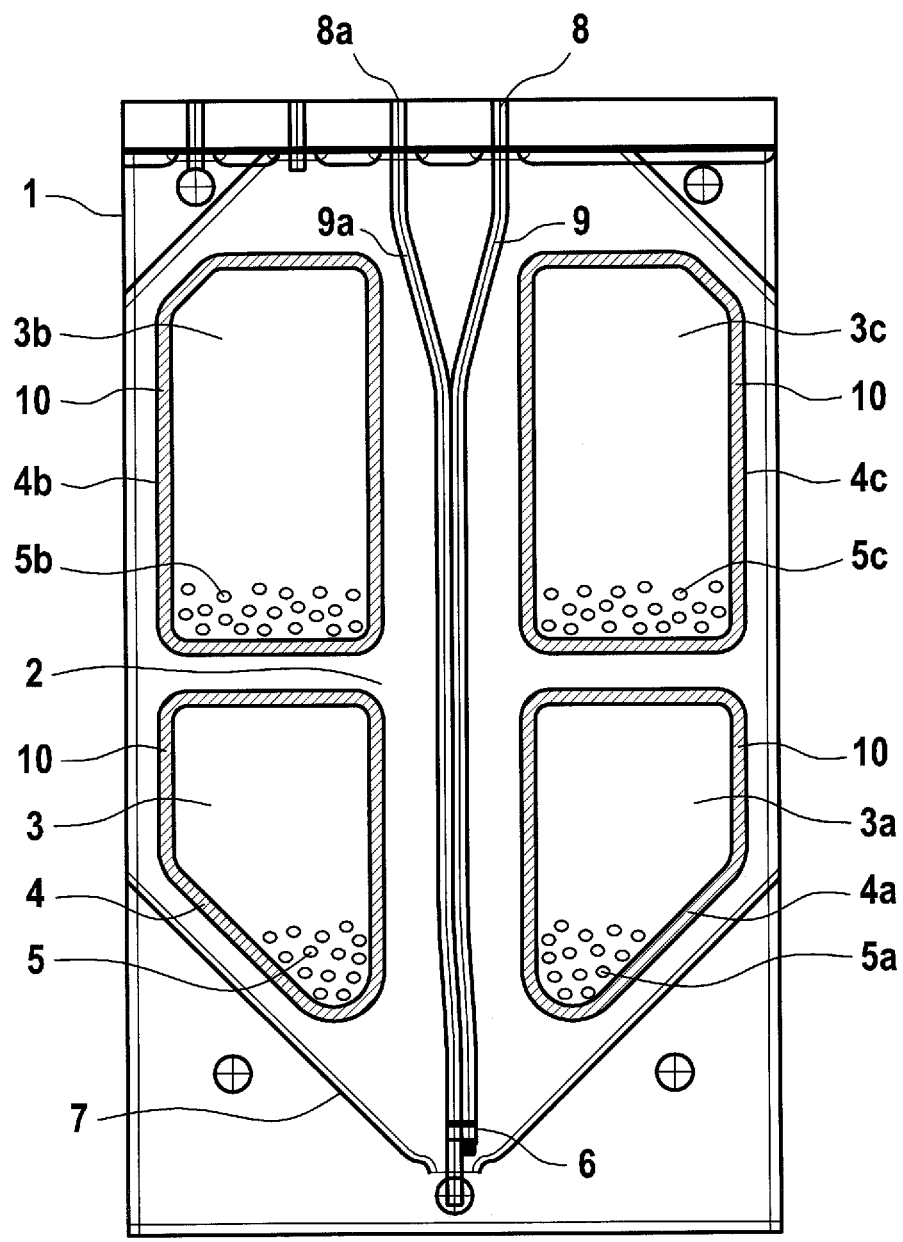
FIG. 6 is a section through a bag which has one type A chamber and four type B chambers, wherein the separating device is present in the form of a tear seam; and, FIG. 7 is a section through a bag which has one type A chamber and four type B chambers, wherein the separating device is present in the form of a tear seam.

FIG. 6 shows a section through a bag (1) which has one type A chamber (2) and four type B chambers (3, 3a, 3b, 3c), wherein separating devices (4, 4a, 4b, 4c) are present in the form of a tear seam (10). When the type A chamber (2) is being filled with fluid through the pipe or tube (9) through the feed opening (8), a force acts on the tear seams (10), with the result these open and firstly the concentrates (5, 5a) of the lower type B chambers (3, 3a) are dissolved first in the fluid introduced into the type A chamber (2) and the concentrates (5b, 5c) of the type B chambers (3b, 3c) are dissolved second in the fluid as a result of the tearing open of the tear seam (10) of these chambers. The pipe or the tube (9) which leads into the type A chamber (2) has, at the lower end of the V-shaped area of the bag, a spray nozzle (6) which ensures the better dissolution of the concentrates (5, 5a, 5b, 5c) in the fluid. Also, this bag (1) preferably has, in the lower area, a conical or V-shaped tapering end which is achieved by welding the inner opposite sides of the bag by a welded seam (7). This welded seam can be a tear seam within the meaning of the invention, which splits open under a corresponding pressure acting as a result of the pouring in of the fluid, with the result that a square bag forms, or a solid welded seam, whereby the V shape of the bag is preserved during the dissolution of the concentrates. The type B chamber (3) preferably contains a concentrate (5) which does not contribute to the electric conductivity of the resulting fluid. The type B chamber (3a) preferably contains a concentrate of the acid component (5a). The type B chambers (3b, 3c) preferably both contain concentrates of the basic component (5b, 5c). The bag further contains a container surrounding the bag according to the invention. It is preferred that such a container surrounding the bag according to the invention is likewise a film bag which surrounds the whole of the outside of the bag according to the invention. A feed opening (8a) for the used dialysis fluid into the surrounding bag preferably leads through a tube (9a) through the inlet or outlet opening of the bag according to the invention all the way through the type A chamber and ends in the bag surrounding the bag according to the invention which is to collect the used dialysis fluid. Preferably, the bag surrounding the bag according to the invention, which is to collect the used dialysis fluid, is made from the same material as the bag according to the invention. The type B chambers (3, 3a, 3b, 3c) are formed by a tear seam which is wholly formed by welding the inner opposite sides of the bag.

Figure 7:
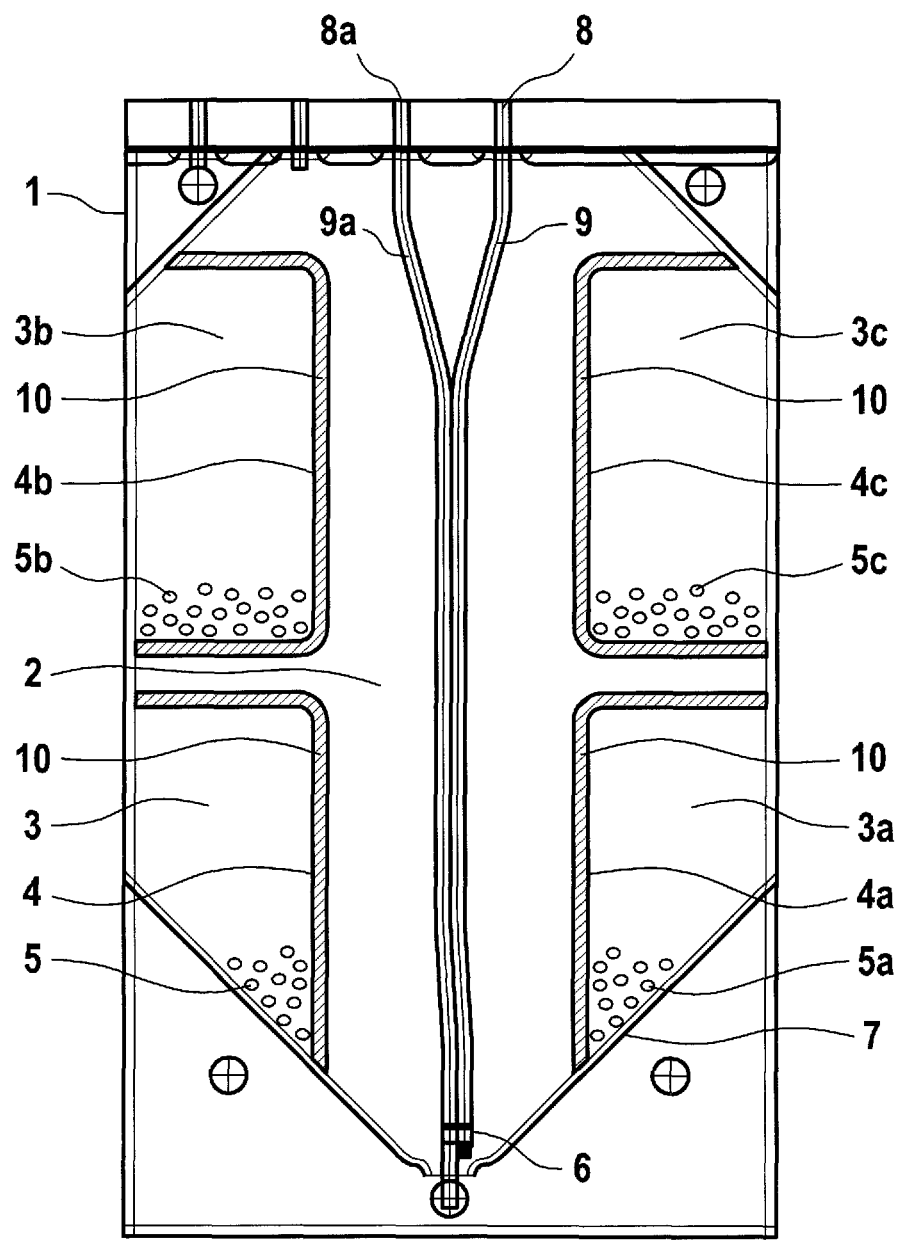

FIG. 7 shows a section through a bag (1) which has one type A chamber (2) and four type B chambers (3, 3a, 3b, 3c), wherein separating devices (4, 4a, 4b, 4c) are present in the form of a tear seam (10). When the type A chamber (2) is being filled with fluid through the pipe or tube (9) through the feed opening (8), a force acts on the tear seams (10), with the result these open and firstly the concentrates (5, 5a) of the lower type B chambers (3, 3*a*) are dissolved first in the fluid introduced into the type A chamber (2) and the concentrates (5*b*, 5*c*) of the type B chambers (3*b*, 3*c*) are dissolved second in the fluid as a result of the tearing open of the tear seam (10) of these chambers. The pipe or the tube (9) which leads into the type A chamber (2) has, at the lower end of the V-shaped area of the bag, a spray nozzle (6) which ensures the better dissolution of the concentrates (5, 5*a*, 5*b*, 5*c*) in the fluid. Also, this bag (1) preferably has, in the lower area, a conical or V-shaped tapering end which is achieved by welding the inner opposite sides of the bag by a welded seam (7). This welded seam can be a tear seam within the meaning of the invention, which splits open under a corresponding pressure acting as a result of the pouring in of the fluid, with the result that a square bag forms, or a solid welded seam, whereby the V shape of the bag is preserved during the dissolution of the concentrates. The type B chamber (3) preferably contains a concentrate (5) which does not contribute to the electric conductivity of the resulting fluid. The type B chamber (3*a*) preferably contains a concentrate of the acid component (5*a*). The type B chambers (3*b*, 3*c*) preferably both contain concentrates of the basic component (5*b*, 5*c*). The bag further contains a container surrounding the bag according to the invention. It is preferred that such a container surrounding the bag according to the invention is likewise a film bag which surrounds the whole of the outside of the bag according to the invention. A feed opening (8*a*) for the used dialyse fluid into the surrounding bag preferably leads through a tube (9*a*) through the inlet or outlet opening of the bag according to the invention all the way through the type A chamber and ends in the bag surrounding the bag according to the invention which is to collect the used dialysis fluid. Preferably, the bag surrounding the bag according to the invention, which is to collect the used dialysis fluid, is made from the same material as the bag according to the invention. The type B chambers (3, 3*a*, 3*b*, 3*c*) are formed by a tear seam which is partly formed by welding the inner opposite sides of the bag.

EXAMPLES

Example 1

Production of a Multi-Chamber Bag with Granular Material

A multilayer film of the above-named film type 1 with the external dimensions 45 cm×66 cm is folded in half on its width side, with the result that two sides of the film are opposite each other and form a two-layer film with rectangular cross-sections (giving a bag size of 45 cm×33 cm), which are joined together at their length sides. 5 cm from the lower edge (width side) and approx. 1 cm from the right edge (length side), the first half of a first granular material (see below for quantity and composition) is introduced into a first pouch by forming a circular linear peel seam (φ12 cm) between the two film inner sides by thermal welding, with the result that the granular material is enclosed by the peel seam. In the same way, the second half of the first granular material is introduced into a second pouch at a distance of approx. 1 cm from the other length side. In the same way, a second granular material (see below for quantity and composition) is introduced into a third pouch at a distance of 3 cm from the peel seam of the first pouch in the direction of the opposite width side and at a distance of approx. 1 cm from the length side (right side). Again 3 cm from the peel seam of the second pouch in the direction of the opposite width side and approx. 1 cm from the length side (left side), a third granular material (see below for quantity and composition) is introduced into this fourth pouch in the same way. The two film halves are then welded together on the three remaining open sides, wherein a gap (approx. 3 cm) is left on the width side opposite the first pouch in the center of the edge and a further gap on the width side opposite this width side on the edge, in the case of which the two film halves are in each case not welded together. A first plastic tube approx. 40 cm long which has a spray nozzle on the inner end and ends inside the bag is passed into the inside of the bag through this gap. A second plastic tube approx. 48 cm long is passed through the inside of the bag through both gaps, with the result that it protrudes from the gaps on both width sides. Tubes and bag films are then welded together at the point of the bag at which the plastic tubes enter the bag and the second plastic tube emerges, such that the inside of the bag is still connected to the outside of the bag only through the first tube. From the center of the lower width side of the bag, two welded seams are also attached in the shape of a V at a 60° angle to each other up to the length sides by thermal welding, with the result that the inside of the bag tapers conically at the lower end (FIG. 5 shows a bag according to example 1). A second bag measuring 48 cm×34 cm, which is welded so that its interior can be entered only through the second tube, is attached around the whole bag. The inside of the second pouch is to serve as collection container for recycled used dialysis fluid.

| | | |
|---|---|---|
| First granular material (half each in the first and second pouch): | NaCl: | 166.78 g |
| | NaHCO$_3$: | 190.34 g |
| Second granular material: | NaCl: | 166.78 g |
| | glucose × H$_2$O: | 68.20 g |
| Third granular material: | salt composition: | 77.38 |
| Composition of the salt composition: | NaCl: | 46.83 wt.-% |
| | KCl: | 11.95 wt.-% |
| | CaCl$_2$ × 2H$_2$O: | 17.67 wt.-% |
| | MgCl$_2$ × 6H$_2$O: | 8.15 wt.-% |
| | citric acid: | 15.40 wt.-% |

Comparison Example 1

A bag is produced substantially as in example 1, except that none of the three pouches is formed, but the three granular materials (first to third granular material according to the example) are introduced directly into the main chamber of the bag.

Comparison Example 2

A bag is produced as in example 1 except that the first granular material is introduced into the third pouch and the third granular material into the first pouch.

Example 2

A multilayer film of the type specified in example 1 with the external dimensions 45 cm×66 cm is folded in half on its width side (giving a bag size of 45 cm×33 cm), with the result that two sides of the film are opposite each other and form a two-layer film with rectangular cross-sections, which are joined together on their length sides.

Approx. 3 cm from the lower edge of one of the width sides, a first granular material (see example 1 for quantity and composition) is introduced into a first pouch by forming a circular linear peel seam (0 approx. 10 cm) between the two film inner sides by thermal welding, with the result that the granular material is enclosed by the two opposite film sides and the peel seam. The center of the first pouch is at approximately the same distance from both length sides; the same also applies for the second and third pouches. In the same way, a second granular material (see example 1 for quantity and composition) is introduced into a second pouch at a distance of approx. 5 cm from the peel seam of the first pouch in the direction of the opposite width side. Again approx. 5 cm from the peel seam of this second pouch in the direction of the opposite width side, a third granular material (see example 1 for quantity and composition) is introduced into a third pouch in the same way. The two film halves are then welded together on the three remaining open sides, wherein a first gap (approx. 3 cm) is left on the width side opposite the first pouch in the center of the edge, in the case of which the two film halves are not welded together. Likewise, a second gap of approx. 2 cm is left on the opposite width side. A 45-cm long first plastic tube which has a spray nozzle on the inner end is passed through this first gap, into the inside of the bag. This end is located inside the bag. A second plastic tube is also passed through the inside of the bag but emerges at the gaps at both ends in equal parts. Tubes and bag films are then welded together at the points of the bag at which the plastic tube(s) enters/emerges from the bag, such that the inside of the bag is still connected to the outside of the bag only through the first feed tube. From the center of the lower width side of the bag, two welded seams are also attached in the shape of a V at a 60° angle to each other up to the length sides by thermal welding, with the result that the inside of the bag tapers conically at the lower end (FIG. 5 shows a bag according to example 1). A second bag measuring 48 cm×34 cm, which is welded so that its interior can be entered only through the second tube, is attached around the whole bag. The inside of the second pouch is to serve as collection container for recycled used dialysis fluid.

Example 3

In example 3, RO water is introduced into the bag at a rate of approx. 6 liters per minute through the feed tube of the bag produced in example 2. The peel seam of the first pouch opens first, whereby the first granular material is gradually dissolved. Next, the peel seam of the second pouch is loosened by the filling pressure caused by filling with fluid. Once the second granular material has gradually dissolved in the RO water, the peel seam of the third pouch opens. The third granular material is then gradually dissolved. After the addition of 60 liters of RO water, there is an almost clear solution, the pH of which is 7.3. Only minor precipitations are to be observed.

Comparison Example 3

In comparison example 3, the procedure is as per example 3, but using the bag produced in comparison example 1. During the filling of the bag, it is noticeable that the mixed granular material (first to third granular material from example 1) dissolves only poorly. In addition, a bubbling is observed which is identified as $CO_2$. At the end of the addition, there is a cloudy solution which has a pH of 8.5. The precipitates contain $CaCO_3$. The concentrate changes color and agglutinates. A storage stability is thus not ensured. After approx. two weeks storage at 40° C. and 75% relative humidity, the glucose and the bicarbonate decompose.

Comparison Example 4

In comparison example 4, the procedure is as per example 3, but using the bag produced in comparison example 2. During the filling of the bag, it is noticeable that the third and the second granular material dissolve well. After the loosening of the peel seam of the third pouch, the first granular material is gradually added. A bubbling begins initially. The bubbles are identified as $CO_2$. The first two thirds of the first granular material are then dissolved completely. However, if the last third of the first granular material enters the solution of the main chamber, it can be observed that the solution clouds slightly initially. In the course of time, the clouding increases. At the end of the addition, there is a strongly clouded mixture which has a pH of 8.6. The precipitates contain $CaCO_3$.

In example 3 and comparison examples 3 and 4, the bags produced in example 1 and comparison examples 1 and 2 were filled with the RO water within 2 hours after production. When carrying out comparison example 4, it is noticeable that the dissolving time of the concentrates is much longer compared with the examples according to the invention and thus not acceptable for the use according to the invention.

Example 4

The bag produced according to example 2 was stored for 3 weeks at a temperature of 40° C. and a humidity of 75%. No visual change in the granularity/powderiness of the three granular materials was able to be observed. After the addition of 60 liters of RO water as in example 3, the same result was achieved as in example 3.

Comparison Example 5

The bag produced according to comparison example 2 was likewise stored for 3 weeks at a temperature of 40° C. and a humidity of 75%. When 60 L RO water was added as in comparison example 3, it was observed that the dissolution behavior of the mixed granular material was greatly reduced. After the addition of 60 liters of RO water, there was a cloudy solution with a large quantity of undissolved concentrate.

Example 5

Production of a Multi-Chamber Bag According to FIG. 6

A multilayer film of the above-named film type 1 with the external dimensions 45 cm×66 cm is folded in half on its width side, with the result that two sides of the film are opposite each other and form a two-layer film with rectangular cross-sections (giving a bag size of 45 cm×33 cm), which are joined together at their length sides. In approximately the dimensions shown in FIG. 6, four chambers (3, 3a, 3b, 3c) are formed by welding tear seams as shown in FIG. 6, surrounding the concentrates (5, 5a, 5b, 5c) in the form of granulates. The two film halves are then welded together on the three remaining open sides, wherein a gap (approx. 3 cm) is left on the width side opposite the first pouch in the center of the edge and a further gap on the width side opposite this width side on the edge, in the case of which the two film halves are in each case not welded together. A first plastic tube approx. 40 cm long which has a spray nozzle on the inner end and ends inside the bag is passed into the inside of the bag through this gap. A second plastic tube approx. 48 cm long is passed through the inside of the bag through both gaps, with the result that it protrudes from the gaps on both width sides. Tubes and bag films are then welded together at the point of the bag at which the plastic tubes enter the bag and the second plastic tube emerges, such that the inside of the bag is still connected to the outside of the bag only through the first tube. From the center of the lower width side of the bag, two welded seams are also attached in the shape of a V at a 60° angle to each other up to the length sides by thermal welding, with the result that the inside of the bag tapers conically at the lower end. A second bag measuring 48 cm 34 cm, which is welded so that its interior can be entered only through the second tube, is attached around the whole bag. The inside of the second pouch is to serve as collection container for recycled used dialysis fluid.

Concentrate (5): glucose (anhydrous): 62 g, resulting concentration: 5.55 mmol/l;

Concentrate (5a): $MgCl_2 \times 6H_2O$: 6.3 g, resulting concentration: 0.5 mmol/l; $CaCl_2$ (anhydrous): 8.62 g, resulting concentration: 1.25 mmol/l; KCl: 9.24 g, resulting concentration: 2 mmol/l; Citric acid: 11.97 g, resulting concentration: 1 mmol/l;

Concentrates (5b, 5c): NaCl: 391.2 g, resulting concentration: 108 mmol/l; $NaHCO_3$: 166.78 g, resulting concentration: 32 mmol/l Example 6

In example 6, RO water is introduced into the bag at a rate of approx. 6 liters per minute through the feed tube of the bag produced in example 5. The peel seam of chambers (3 and 3a) opens first at the same time, whereby the concentrates (5 and 5a) are gradually dissolved. Next, the peel seams of the chambers (3b and 3c) is loosened by the filling pressure caused by filling with fluid. The concentrates (5b and 5c) are then gradually dissolved. After the addition of about 60 to 62 liters of RO water, there is a total clear solution the pH of which is 7.3. No precipitations are to be observed.

Example 7

During the introduction of water in example 6 the electric conductivity of the fluid in the bag is measured. Before the opening of the bags the conductivity measured is about 0 mS/cm. When the second type B chamber (3a) is opened, a change of the conductivity of the fluid introduced is measured. Since the peel seam strength of the peel seam of the chambers (3) and (3a) is similar, both concentrates (5) and (5a) are dissolved at the same time. Since the concentrate (5a) leads to a change in conductivity and due to the release of concentrates (5) and (5a) at the same time, it can be ensured that glucose is dissolved in the fluid.

It is understood that the foregoing description is that of the preferred embodiments of the invention and that various changes and modifications may be made thereto without departing from the spirit and scope of the invention as defined in the appended claims.

What is claimed is:

1. A method of dissolving/mixing a concentrate in/with a fluid, comprising:
    (a) providing a concentrate in one of several chambers of a multi-chamber film bag, wherein the chambers of the multi-chamber film bag are separated from each other by a separating device;
    (b) introducing a fluid into one of the chambers;
    (c) breaching of the separating device between the chambers by the introducing the fluid; and
    (d) dissolving/mixing the concentrate in/with the fluid, wherein the film is a flexible, extendible film,
    wherein a ratio of a volume capacity of the multi-chamber film bag when filled to its maximum, to the volume capacity in the state in which the multi-chamber film bag film is unextended, is ≥3/1,
    wherein a bottom section of the multi-chamber film bag is formed as a cone with a cone-angle of from 30° to 75°,
    wherein the cone is formed by the separating device, which breaches at a pre-determined pressure caused by the introduction of the fluid so that a rectangular bag is formed, and
    wherein the separating device is a peel seam that has a peel seam strength in the range of from 0.2 to 15 N/15 mm.

2. The method according to claim 1, wherein the concentrate is provided in a type B chamber of the multi-chamber film bag, wherein the multi-chamber film bag comprises at least one type A chamber and at least one type B chamber.

3. A method for the production of a medical fluid comprising:
    (a) providing a multi-chamber film bag comprising a type A chamber, a first type B chamber, and a second type B chamber,
    wherein the first type B chamber comprises a first concentrate that does not contribute to the electrical conductivity of the medical fluid, and the second type B chamber comprises a second concentrate that contributes to the electrical conductivity of the medical fluid, and wherein the first type B chamber and the second type B chamber are each separated from the type A chamber by separating devices;
    (b) introducing a fluid into the type A chamber;
    (c) breaching of the separating devices between the chambers by the introducing the fluid; and
    (d) dissolving/mixing of the concentrates in/with the fluid,
    wherein, by the introducing the fluid, the separating device of the first type B chamber is breached before or at the same time as the separating device of the second type B chamber is breached,
    wherein the film is a flexible, extendible film,
    wherein the ratio of a volume capacity of the multi-chamber film bag when filled to its maximum, to the volume capacity in the state in which the multi-chamber film bag film is unextended, is ≥3/1,
    wherein a bottom section of the multi-chamber film bag is formed as a cone with a cone-angle of from 30° to 75°,
    wherein the cone is formed by the separating device, which breaches at a pre-determined pressure caused by the introduction of the fluid so that a rectangular bag is formed, and
    wherein the separating device is a peel seam that has a peel seam strength in the range of from 0.2 to 15 N/15 mm.

4. The method according to claim 2, wherein the multi-chamber film bag comprises at least one further type B chamber that is separated from each of the other chambers of the bag by one or more further separating devices.

5. The method according to claim 4, wherein the one or more further separating devices are breached by the introducing the fluid.

6. The method according to claim 4, wherein the at least one further type B chamber contains at least one further concentrate.

7. The method according to claim 2, wherein the separating device between the at least one type A chamber and the at least one type B chamber is formed into a peel seam by welding together two opposite inner side walls in the multi-chamber film bag.

8. The method according to claim 7, wherein the at least one type B chamber comprises a first type B chamber and a second type B chamber, the separating device comprises a first separating device and a second separating device, the first separating device has a first peel seam and separates the at least one type A chamber from the first type B chamber, the second separating device has a second peel seam and separates the at least one type A chamber from the second type B chamber, and the peel seam strength of the peel seam of the first separating device is equal to or lower than the peel seam strength of the peel seam of the second separating device.

9. The method according to claim 2, wherein the at least one type B chamber is formed by an inner bag inside the type A chamber.

10. The method according to claim 9, wherein the inner bag comprises a wall and a peel seam present on the wall, and the breaching of the separating device takes place by peeling open the peel seam present on the wall of the inner bag.

11. A multi-chamber film bag comprising at least two different concentrates in different chambers defined by a separating device,
wherein the film is a flexible, extendible film,
wherein a ratio of a volume capacity of the multi-chamber film bag when filled to its maximum, to the volume capacity in the state in which the multi-chamber film bag film is unextended, is ≥3/1,
wherein a bottom section of the multi-chamber bag is formed as a cone with a cone-angle of from 30° to 75°,
wherein the cone is formed by the separating device and the separating device breaches at a pre-determined pressure caused by the introduction of the fluid so that a rectangular bag is formed, and
wherein the separating device is a peel seam that has a peel seam strength in the range of from 0.2 to 15 N/15 mm.

12. The multi-chamber film bag according to claim 11, further comprising one type A chamber and at least one type B chamber, wherein one of the concentrates is present in the type A chamber and the other in the at least one type B chamber, or both concentrates are each present in the at least one type B chamber.

13. The multi-chamber film bag according to claim 11, wherein the different chambers comprise one type A chamber, a first type B chamber, and a second type B chamber, the at least two different concentrates comprise a first concentrate and a second concentrate, the first type B chamber comprises the first concentrate, the first concentrate is not able to contribute to the electrical conductivity of a fluid, the first concentrate is dissolved, the second type B chamber comprises the second concentrate, the second concentrate is able to contribute to the electrical conductivity of a fluid, and the second concentrate is dissolved.

14. The multi-chamber film bag according to claim 11, wherein the peel seam is formed by welding together two opposite inner side walls of the multi-chamber film bag.

15. The multi-chamber film bag according to claim 12, wherein the at least one type B chamber is formed by an inner bag inside the type A chamber.

16. A method of keeping dialysis fluid in a haemodialysis or peritoneal dialysis device, comprising providing the multi-chamber film bag according to claim 11 as a container.

17. The method of claim 1, wherein the peel seam strength is in the range of from 0.5 to 8 N/15 mm.

18. The method of claim 3, wherein the peel seam strength is in the range of from 0.5 to 8 N/15 mm.

19. The multi-chamber film bag of claim 11, wherein the peel seam strength is in the range of from 0.5 to 8 N/15 mm.

* * * * *